United States Patent [19]

De Vuono et al.

[11] Patent Number: 4,989,595
[45] Date of Patent: Feb. 5, 1991

[54] ASPIRATOR/NEBULIZER

[75] Inventors: Anthony C. De Vuono; Richard Razgaitis, both of Columbus, Ohio

[73] Assignee: Battelle Development Corporation, Columbus, Ohio

[21] Appl. No.: 110,640

[22] Filed: Oct. 14, 1989

Related U.S. Application Data

[63] Continuation of Ser. No. 778,838, Sep. 23, 1985, abandoned.

[51] Int. Cl.$^5$ ............................................. A61M 16/00
[52] U.S. Cl. ......................... 128/200.017; 128/203.12; 128/204.25
[58] Field of Search ..................... 128/200.14, 200.17, 128/200.18, 201.28, 203.12–204.18, 204.21, 204.24, 204.25, 205.18, 205.19, 205.24, 205.25, 205.11

[56] References Cited

U.S. PATENT DOCUMENTS

| Re. 23,496 | 5/1952 | Seeler | 128/204.25 |
| 3,485,243 | 12/1969 | Bird et al. | 128/205.24 |
| 3,507,297 | 4/1970 | Dann | 128/205.24 |
| 3,863,638 | 2/1975 | Cavallo | 128/204.21 |

FOREIGN PATENT DOCUMENTS

| 893998 | 9/1954 | Fed. Rep. of Germany. |
| 692113 | 7/1965 | Italy | 128/200.17 |

Primary Examiner—Max Hindenburg
Assistant Examiner—John P. Lacyk
Attorney, Agent, or Firm—Barry S. Bissell

[57] ABSTRACT

A respiratory care device utilizes pressurized oxygen to pump an oxygen/air mixture to the patient. The device comprises a coupled turbine and blower. The pressurized oxygen drives the turbine which pumps air through the blower. The oxygen may be mixed with the air in selected ratios and delivered to the patient. Droplets may be added to the oxygen, to the air or to the mixture, upstream or downstream of the device or within the device.

5 Claims, 2 Drawing Sheets

ASPIRATOR/NEBULIZER

This is a continuation of co-pending application Ser. No. 778,838 filed on 09-23-85 now abandoned.

BACKGROUND OF THE INVENTION

Current inhalation therapy requirements vary over a wide range. For example, high-oxygen concentration streams are occasionally required for short durations, but the longer term care generally demands low oxygen gas. But the total gas volume needs of the patient (air plus oxygen) remains nearly constant. These broad requirements necessitate an aspirator device with a high degree of flexibility in effecting the desired composition and flow rate.

Moreover, moderate back pressures caused by patient exhalation together with the use of long, small-diameter delivery tubes could beneficially be overcome by a device capable of providing necessary gas volumes.

SUMMARY OF THE INVENTION

It is an object of the present invention to provide an aspirator which has the flexibility to deliver an air/oxygen mixture at nearly constant volume with an easily selectable composition.

It is a further object to provide a device which can deliver the gas mixture at high or low flow rates.

It is also an object to provide a device for delivering the gas mixture at such pressure as to be able to overcome the back pressures inherent in a patient delivery system using smaller-bore tubing than presently used.

It is finally an object to provide such a device which is of such simplicity and cost that it can be wholly or partly disposable.

In accordance with the objectives, the invention is a method and apparatus for diluting a high-pressure oxygen stream with ambient air.

In its broadest sense, the invention comprises a device for causing high-pressure oxygen to do mechanical work to pump low pressure air and then mixing selected portions of the air and oxygen into a therapeutic mixture.

In a narrower sense, the invention comprises a gas turbine and blower coupled for rotation, means for directing a high-pressure oxygen stream to rotate the tubine, a source of air in communication with the blower such that the air is pumped by the blower upon rotation of the turbine, and means for mixing selectable portions of the oxygen stream and pumped air for delivery to the patient.

DESCRIPTION OF THE INVENTION

It would be desirable in the respiratory care field to be able to deliver large volumes of oxygen or an oxygen/air mixture to a patient at fairly high pressure and a constant composition. Currently the inability to do this has resulted in the use of open patient masks and large diameter corrugated tubes which have a low back pressure. With this apparatus, a flow of 40–60 liters-per-minute (lpm) of gas can reach the patient but only 1–2 lpm are used, the rest is lost out the mask openings. Moreover, since the gas is at fairly low pressure, liquid in the gas may rainout in the patient hose leaving a site for infectious organisms to grow. Antibiotics cannot be added to the gas without contaminating the entire area through the open mask.

The present device provides for the pumping of air or air/oxygen mixture at up to about 50 lpm and a pressure equal to 2–3 inches of water. This enables the use of a medium back pressure closed mask and small diameter delivery tube. The small quantities of gas (e.g. 1–2 lpm) that are genuinely needed can be delivered and maintained "on demand" because of the pressurization capability. The back pressure capability allows small-bore-tubing to be used which results in high gas velocities preventing rainout. It is also now possible to filter the gas (which requires a pressure drop) and to add antibiotics to the patient gas (since it is directed to a closed mask).

In general, the current technology involves using the high pressure (50 psi) oxygen stream in hospital rooms to aspirate air and liquid through venturi action (so called Bernoulli devices). This operation tends to limit oxygen concentration to about 27–28% minimum. The present invention proposes to more directly pump the room air by causing the oxygen to do mechanical work to run an air compressor and then mixing portions of the oxygen with the compressed air. The oxygen concentration could, of course, be reduced to that of the ambient air since no oxygen need be mixed in the final gas.

Figure 1:
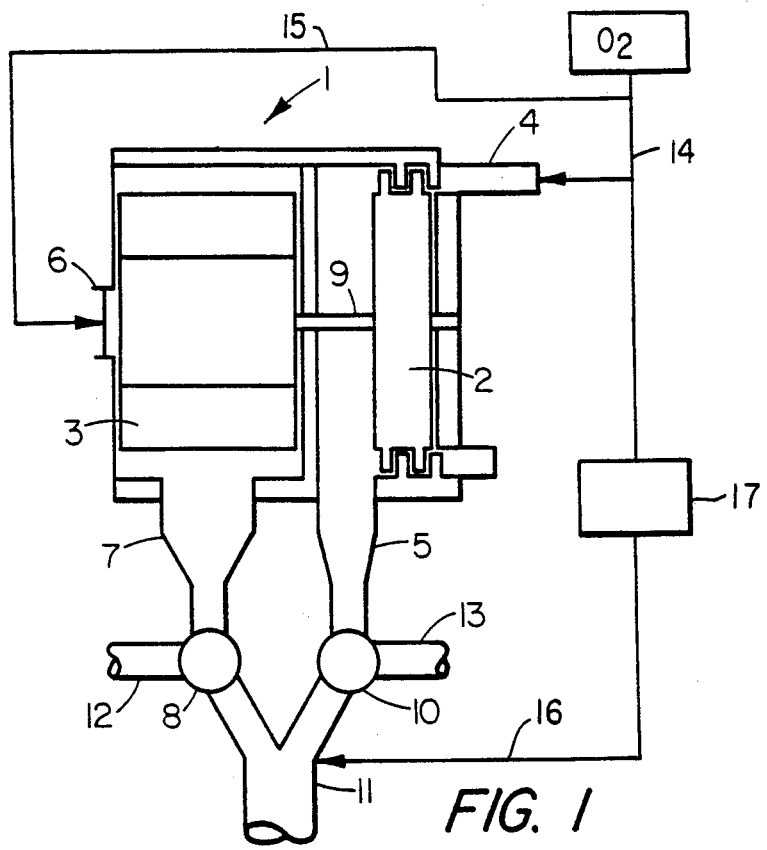
FIG. 1 is a schematic view of the turbine/blower device according to the invention.

FIG. 1 shows a schematic of one embodiment of the invention. The aspirator device 1 comprises an oxygen turbine 2 mounted for rotation with a blower 3 through shaft 9. The turbine may be rotated by impulse or reaction by the oxygen stream entering through an orifice 4 and exiting through outlet 5. An impulse turbine is shown in the Figure. The blower pumps room air through entrance 6 out exit 7. Valve 8 allows a selectable portion of the air to be dumped through line 12 and a selected portion to be directed to the patient through delivery hose 11. Valve 10 allows spent oxygen from the turbine to be dumped through line 13 or delivered to the patient through line 11.

As shown in FIG. 1, a main oxygen stream through line 14 may be valved to provide the first oxygen stream to orifice 4 to run the turbine and a second oxygen stream in line 16 to nebulize liquid droplets in nebulizer 17 for delivery to the air stream downstream of the turbine prior to delivery to the patient. Alternatively, the second oxygen stream can also be optionally separated from the main stream through line 15 and directed into the blower 3, such as through entrance 6 to be mixed with incoming air.

Figure 2:
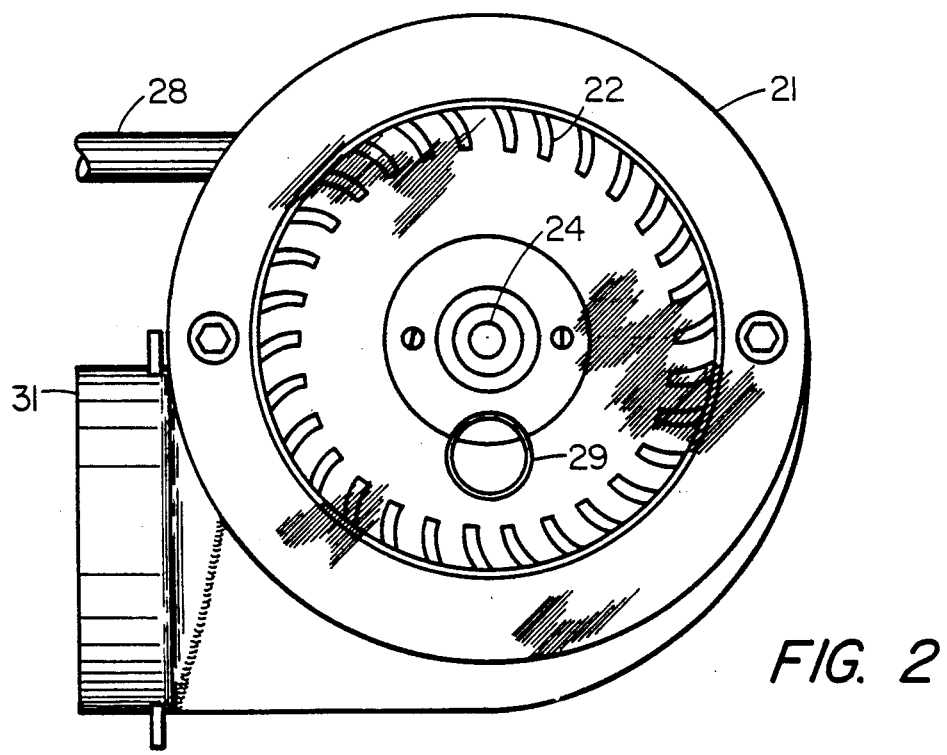
FIG. 2 is a sectional elevation view through the internal parts of the turbine/blower device.
Figure 3:
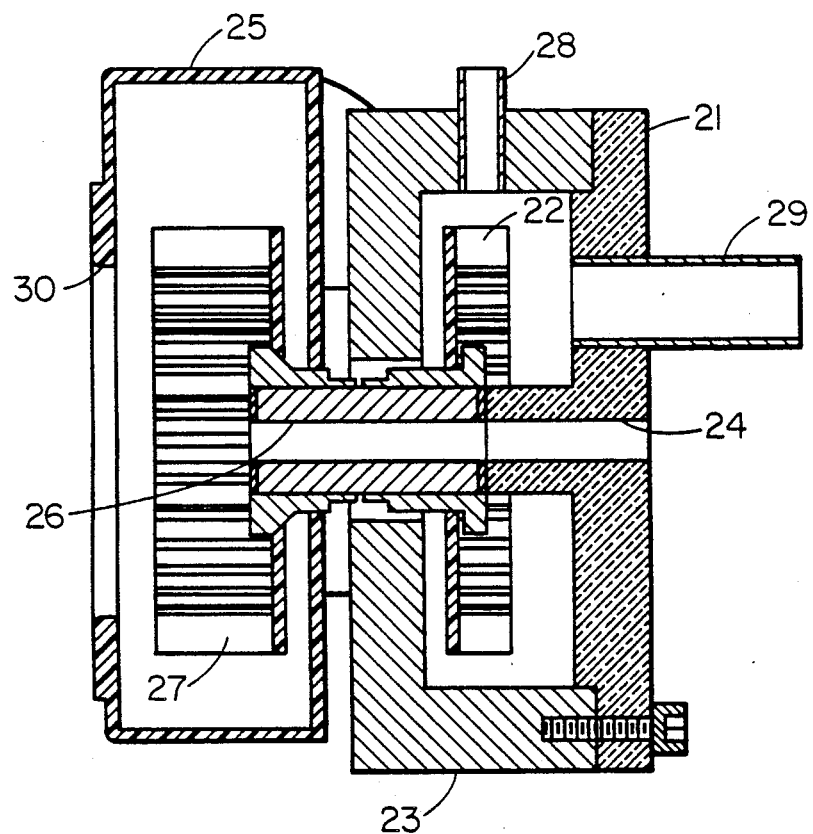
FIG. 3 is a side view of the device in FIG. 2 looking at the turbine.

FIGS. 2 and 3 show more detail of the turbine/blower embodiment. A turbine housing consists of a circular front plate 21 joined to a back container 23. The blower housing 25 is fixed to the back container 23 by convenient means. Shaft 24 is fixed to the front plate and extends axially through the turbine housing into the blower housing. A cylindrical bearing 26 is rotatable on the shaft 24. Turbine 22 and blower 27 are fixed for rotation on the bearing 26.

Oxygen orifice 28 directs the oxygen stream against the turbine blades. Oxygen exit 29 exhausts the spent oxygen. Air entrance 30 on the blower housing is in communication with room air to pump air through the device and out air outlet 31.

The turbine is preferably directly coupled to the blower without gears. It preferably has single stage, backward-curved blades though other configurations may also be used. The blower is preferably a conventional, center-draw forward-blade fan. Typically, an orifice 0.2–0.5 mm in diameter can deliver 1–2 lpm oxygen to the turbine and rotate it at up to about 12,000 rpm delivering air at about 50 lpm and 3 inches of water back pressure.

The aspirator is preferably disposable and made of plastic parts (except for the bearings and shaft). In this case oxygen from the turbine could be mixed with the compressed air. Alternatively, the turbine portion may be designed to be reusable, allowing for use of better construction materials. The blower would be disposable since it has direct communication to the patient. In this case, the oxygen to the turbine would be bled from the main oxygen stream (only 1–2 lpm are needed) and any oxygen requirements for mixing with the air would be met with fresh oxygen from the main stream. The main oxygen stream could enter the compressed gas downstream of the blower or could enter the blower with the ambient air at the air inlet.

Liquid or a liquid/medicament mixture may be added at any convenient point. For example, a conventional mist generator could be used to supply moisture to the air inlet on the blower. The main oxygen stream could also be used to lift and nebulize liquid in the conventional way for introduction to the blower air inlet or to the compressed gas downstream of the device as shown in FIG. 1.

The invention has been described particularly with respect to a turbine/blower device. In the broader sense, however, the invention envisions the use of any convenient device for converting the energy in the pressurized oxygen into useful mechanical energy to increase the pressure of low pressure, ambient air. For example, a reciprocating positive displacement pump, pressurized bottle, gear pump, hydraulic multiplier, vibrating membrane, or shear drag turbine could be used in place of the turbine. Unlike conventional Bernoulli the oxygen and air may be kept separate so that air itself may be delivered to the patient under slight pressure or a mixture of air and oxygen may be delivered.

EXAMPLES OF THE PREFERRED EMBODIMENT

An aspirator device such as shown in FIGS. 2 and 3 was constructed. A 7.5 cm diameter turbine with backward-curved, single-stage blades was fixed in a housing. The housing back was made of aluminum while the face plate was a clear polycarbonate. The oxygen nozzle was about 0.4 mm in diameter. The turbine was mounted on a shaft and a porous bronze bearing.

The blower had a 14 CFM output. The impeller was contained in a light polycarbonate housing and coupled to the turbine through the bearing.

Three feet of patient hose (22 mm I.D.) was attached to the air output. The spent oxygen from the turbine was mixed with the compressed air output. Table 1 shows the mixing results.

TABLE 1

| | $O_2$ input (lpm) | Air Output (lpm) | Shaft speed (rpm) | $O_2$ % |
|---|---|---|---|---|
| 1 | 0.5 | 30.1 | 800 | 26.5 |
| 2 | 1.0 | 43.2 | 1148 | 25.8 |
| 3 | 1.3 | 51.4 | 1367 | 25.7 |
| 4 | 1.5 | 56.8 | 1511 | 25.6 |
| 5 | 2.0 | 69.4 | 1844 | 25.8 |
| 6 | 2.5 | 80.2 | 2131 | 26.0 |
| 7 | 2.7 | 85.6 | 2276 | 26.2 |

We claim:

1. A respiratory care device for delivering an oxygen-containing gas under positive pressure to a patient comprising:
    a source of high-pressure oxygen,
    a source of air,
    a rotatable gas turbine,
    a rotatable blower coupled to the gas turbine for rotation therewith and having an air entrance communicating with the source of air to admit the air to the blower and an air exit for discharging the air from the blower,
    means for utilizing at least a first portion of the high-pressure oxygen to rotate the turbine,
    means for delivering the air from the blower air exit to the patient, and
    means for mixing a second portion of the oxygen with the air prior to delivery to the patient.

2. The respiratory care device of claim 1 wherein the first and second portions of the oxygen are separate streams.

3. The respiratory care device of claim 2 wherein the means for mixing the second portion of the oxygen is located upstream of the blower entrance.

4. The respiratory care device of claim 2 wherein the means for mixing the second portion of the oxygen is located downstream of the blower exit.

5. A respiratory care device for delivering an oxygen-containing gas under positive pressure to a patient comprising:
    a source of high-pressure oxygen,
    a source of air,
    a rotatable gas turbine,
    a rotatable blower coupled to the gas turbine for rotation therewith and having an air entrance communicating with the source of air to admit the air to the blower and an air exit for discharging the air from the blower,
    means for utilizing at least a first portion of the high-pressure oxygen to rotate the turbine,
    means for delivering the air from the blower air exit to the patient, and
    means for nebulizing a liquid with a second portion of the high-pressure oxygen and mixing the second portion of oxygen and nebulized liquid with the air downstream of the turbine prior to delivery to the patient.

* * * * *